United States Patent
Hayes-Pankhurst et al.

(10) Patent No.: US 7,621,511 B2
(45) Date of Patent: Nov. 24, 2009

(54) FRAGRANCE DISPENSERS

(75) Inventors: Paul Richard Hayes-Pankhurst, London (GB); Keith Graham Lacy, London (GB); Paul Simon Wells, Wokingham (GB)

(73) Assignee: Carbonate Limited, London (GB)

( * ) Notice: Subject to any disclaimer, the term of this patent is extended or adjusted under 35 U.S.C. 154(b) by 244 days.

(21) Appl. No.: 10/568,069

(22) PCT Filed: Apr. 27, 2004

(86) PCT No.: PCT/GB2004/001754

§ 371 (c)(1),
(2), (4) Date: Feb. 13, 2006

(87) PCT Pub. No.: WO2004/096300

PCT Pub. Date: Nov. 11, 2004

(65) Prior Publication Data

US 2007/0036688 A1    Feb. 15, 2007

(30) Foreign Application Priority Data

Apr. 28, 2003    (GB) ................. 0309624.5

(51) Int. Cl.
*B01F 3/04* (2006.01)
(52) U.S. Cl. .................. 261/30; 261/64.1; 261/65; 261/84; 261/DIG. 88
(58) Field of Classification Search .......... 261/23.1, 261/30, 64.1, 65, 72.1, 74, 84, 125, DIG. 88, 261/DIG. 89
See application file for complete search history.

(56) References Cited

U.S. PATENT DOCUMENTS

| | | | | | |
|---|---|---|---|---|---|
| 3,711,023 | A | * | 1/1973 | Smith | 239/54 |
| 4,603,030 | A | * | 7/1986 | McCarthy | 472/57 |
| 5,023,020 | A | * | 6/1991 | Machida et al. | 261/18.1 |
| 5,167,877 | A | * | 12/1992 | Pai | 261/18.1 |
| 5,259,062 | A | * | 11/1993 | Pelonis | 392/365 |
| 5,565,148 | A | * | 10/1996 | Pendergrass, Jr. | 261/30 |
| 6,234,455 | B1 | * | 5/2001 | Wittek | 261/30 |
| 6,254,065 | B1 | * | 7/2001 | Ehrensperger et al. | 261/26 |
| 6,713,024 | B1 | * | 3/2004 | Arnell et al. | 422/124 |
| 7,036,800 | B2 | * | 5/2006 | Ellis | 261/26 |
| 7,344,123 | B2 | * | 3/2008 | Pankhurst et al. | 261/30 |

FOREIGN PATENT DOCUMENTS

| | | |
|---|---|---|
| GB | 2 118 636 | 11/1983 |
| WO | WO 03/028775 | 4/2003 |

* cited by examiner

*Primary Examiner*—Scott Bushey
(74) *Attorney, Agent, or Firm*—Stites & Harbison PLLC; Douglas E. Jackson

(57) ABSTRACT

A fragrance disperser includes a first source (25) of fragrance associated with a first flowpath (21) and a second source of fragrance (26) associated with a second flowpath (23). A fan (17) provides a flow of air along the first flowpath (21) or the second flowpath (23) to release the associated fragrance. A flow controller (38, 52) is movable by an actuator (34) to open and close the flowpaths (21, 23) so that only one fragrance is released at a time or a proportionate mixture of the two fragrances is released.

24 Claims, 4 Drawing Sheets

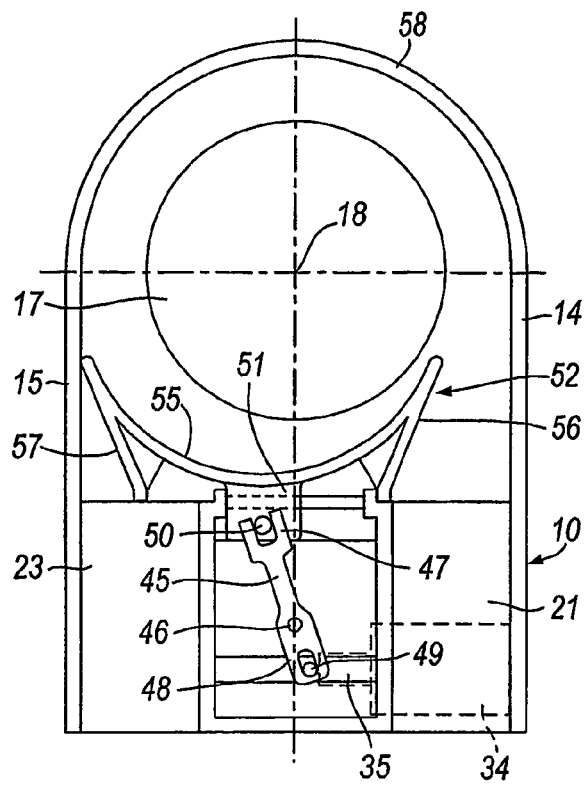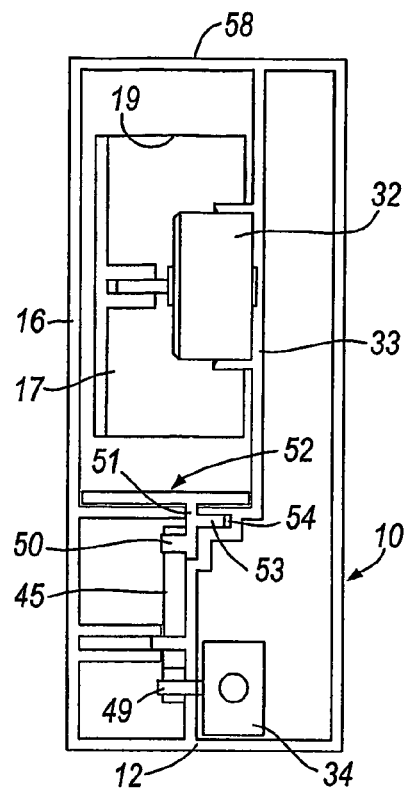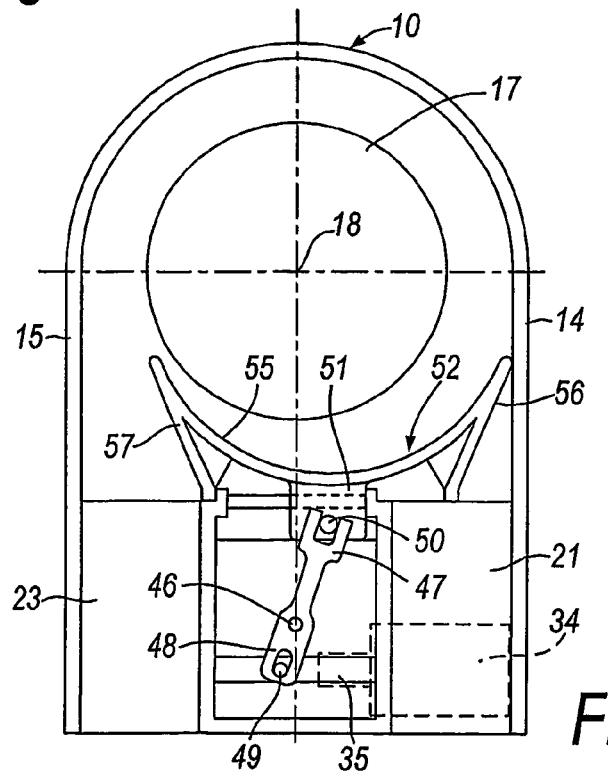

FRAGRANCE DISPENSERS

The invention relates to fragrance dispersers.

Fragrance dispersers are used to release one or more fragrances into an enclosed space such as a room. In general, the fragrance is held by a fragrance source and released either by natural convection or by forced convection or by heating a wick or pad, for example, holding the fragrance.

According to the invention, there is provided a fragrance disperser comprising first and second sources of fragrance, first and second flowpaths, each associated with a respective source of fragrance, a fan for providing a flow of air along the first and second flowpaths to release the associated fragrances and a flow controller movable by an actuator between a first position in which air flows along the first flowpath to allow release of the first fragrance and a second position in which air flows along the second flowpath to allow release of the second fragrance.

Figure 1:
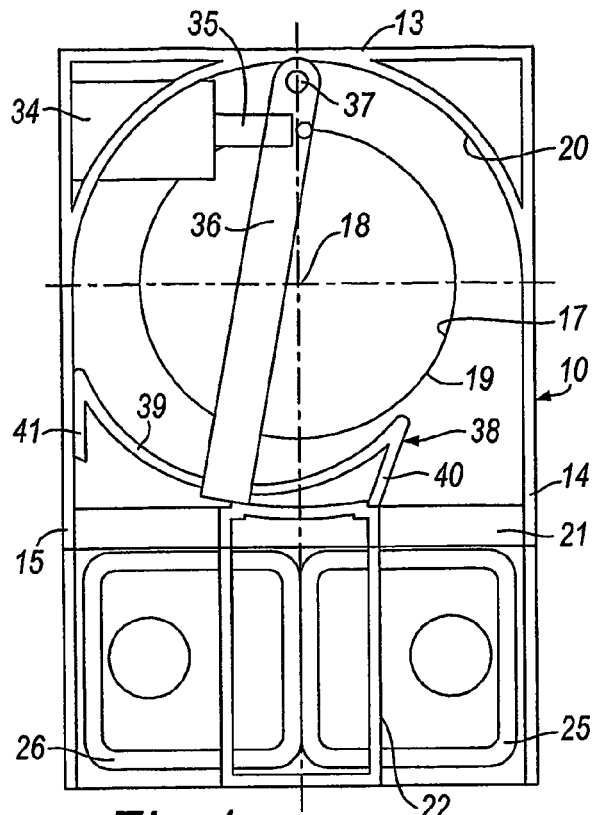
Figure 3:
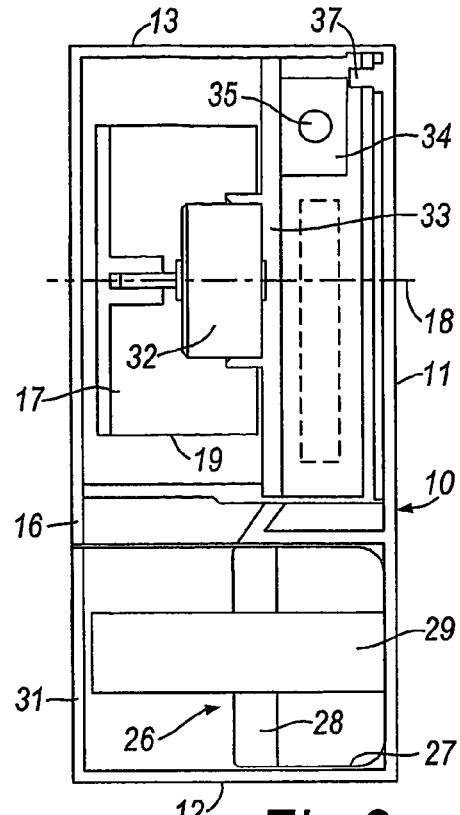
Figure 2:
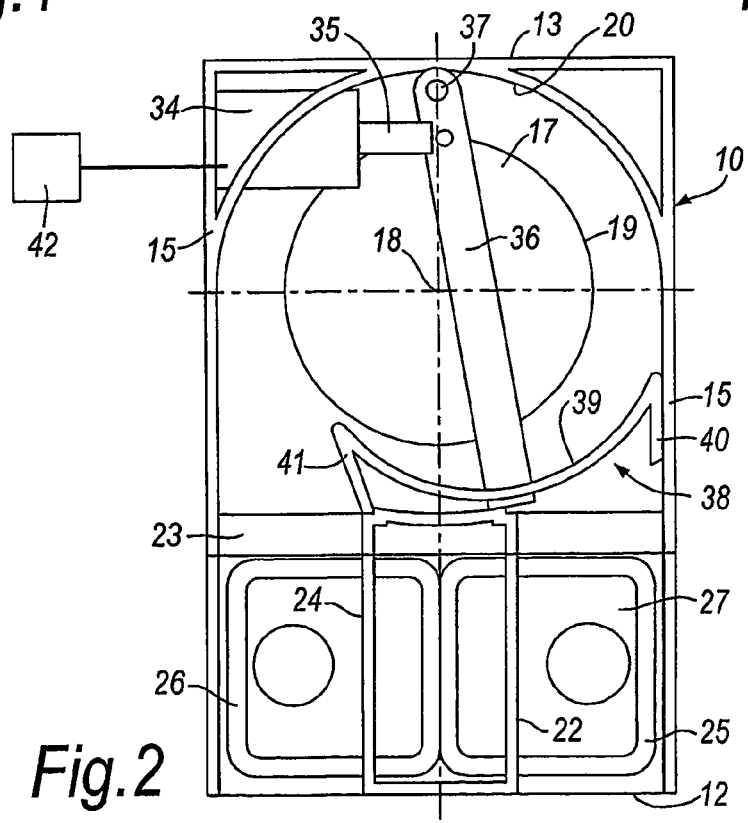
Figure 7:
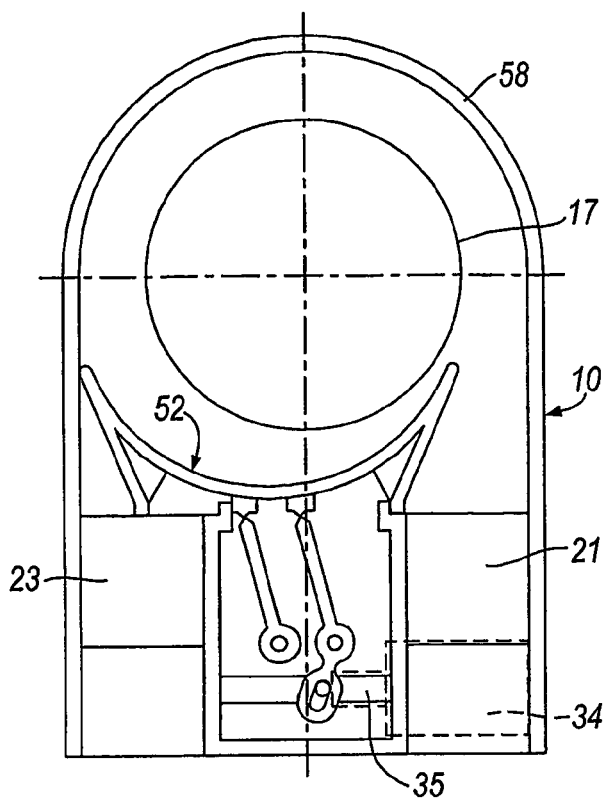
Figure 9:
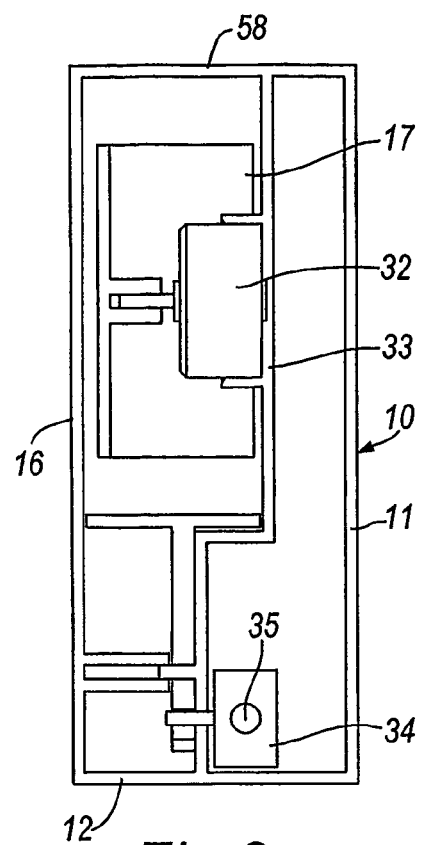
Figure 8:
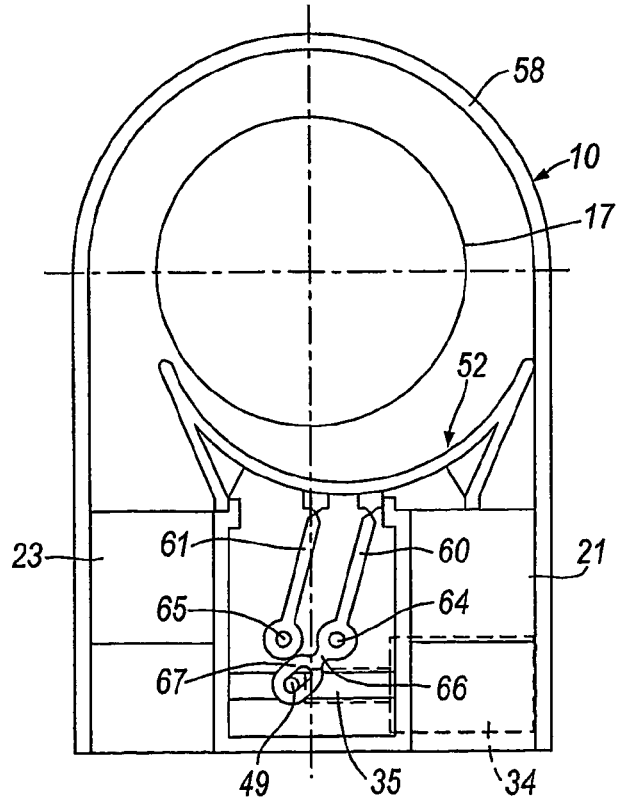
Figure 10:
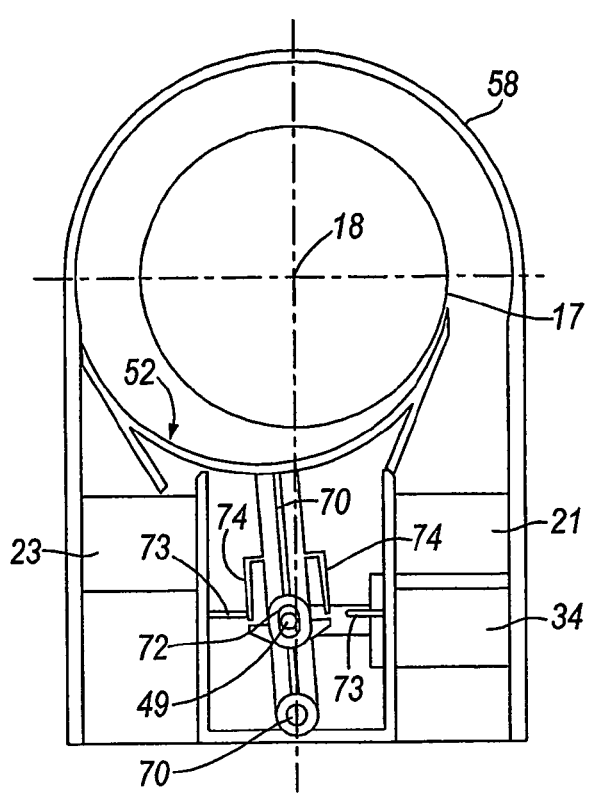
Figure 12:
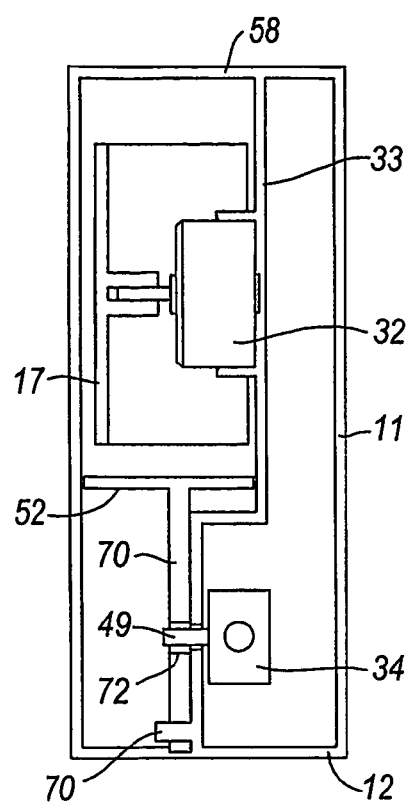
Figure 11:
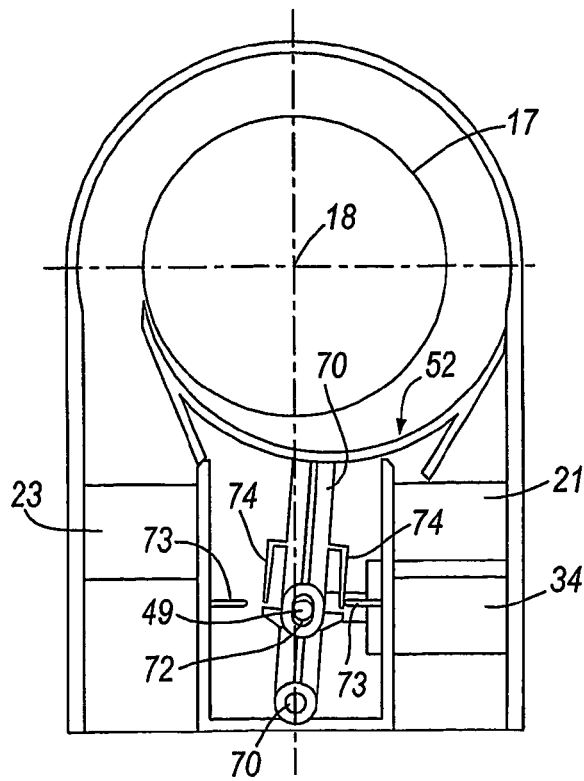

The following is a more detailed description of four embodiments of the invention, by way of example, reference being made to the accompanying drawings in which:

FIG. 1 is a top view of a first form of fragrance disperser with a front cover removed showing a fan, a pivoted shutter in a first position and two passageways including respective sources of fragrance, FIG. 2 is a similar view to FIG. 1, but with the shutter in a second position, FIG. 3 is a side elevation of the first form of fragrance disperser with a side wall removed, and FIG. 4 is a top view of a second form of fragrance disperser with a cover removed showing a fan, a translating shutter in a first position and two passageways, FIG. 5 is a similar view to FIG. 3, showing the shutter in a second position, FIG. 6 is a side elevation of the second form of fragrance disperser with the side wall removed, FIG. 7 is a top view of a third form of fragrance disperser with the front cover removed showing a fan, a pivoted shutter in a first position and two passageways, FIG. 8 is a similar view to FIG. 7 but with the shutter in a second position, FIG. 9 is a side elevation of a third form of fragrance disperser with a side wall removed, FIG. 10 is a top view of a fourth form of fragrance disperser with a cover removed showing a fan, a pivoted shutter in a first position and two passageways, FIG. 11 is a similar view to FIG. 10 but with the shutter in a second position, and FIG. 12 is a side elevation of the fourth form of fragrance disperser with the side wall removed.

Referring first to FIGS. 1 to 3, the first form of fragrance disperser comprises housing 10 formed by a generally rectangular base 11 (see FIG. 3) surrounded by a back wall 12, a front wall 13 and first and second side walls 14,15. The top of the housing is closed by a cover 16 seen in FIG. 3.

A fan 17 is mounted within the housing rotatable about an axis 18 normal to the base 11. The fan 17 has an outer periphery 19 and is of any suitable conventional type. The interior of the housing is provided with an arcuate wall 20 extending between the first side wall 14, the front wall 13 and the second side wall 14 and defining a chamber which receives the fan 17. The first side wall 14 continues from one end of the arcuate wall 20 and forms one wall of a first passage 21. The remainder of the passage 21 is formed by a portion of the base 11, a portion of the cover 16 and a first interior wall 22 extending from the back wall 12 parallel to the side walls 14,15 towards the fan 17. This is best seen in FIGS. 1 and 2.

Likewise, the second side wall 15 extends from the other end of the arcuate wall 20 to form a wall of a second passage 23. The other walls of the second passage are formed by portions of the base 11 and the cover 16 and by a second interior wall 24 extending from the back wall 12 parallel to the side walls 14,15 towards the fan 17.

The first passage 21 contains a first fragrance bottle 25 and the second passage 23 contains a second fragrance bottle 26. As seen in FIG. 3, each fragrance bottle 25,26 comprises a container 27 containing the fragrance with a cover 28 through which extends a wick 29. The portion of the wick 29 beyond the cover 28 therefore lies in the associated passage 21,23. The first passage 21 includes a first outlet 30 and the second passageway 23 includes a second outlet 31.

As seen in FIG. 3, the fan 17 is driven by an electric motor 32 about the axis 18. The motor 32 is carried on an inner dividing wall 33 (see FIG. 3) of the housing 10 located between the base 11 and the cover 16 and extending generally parallel to the base 11. The fan 11 is on the cover side of this wall and an actuator 34 is located between the dividing wall 33 and the base 11 (see FIG. 3). The actuator 34, which is preferably an electrically operated solenoid, has an output rod 35, best seen in FIGS. 1 and 2, which is movable between first and second positions. An arm 36 is rotatably mounted at one end on a fixed pivot 37 adjacent the front wall 13 for movement about an axis parallel to the fan axis 18. The arm 36 extends behind the fan 17 and is fixed at its opposite end to a flow controller in the form of a shutter 38. The shutter 38, as best seen in FIGS. 1 and 2, includes a generally arcuate wall 39 having an axis coaxial with the pivot 37. The arcuate wall 39 has a first extension surface 40 at one end and a second extension surface 41 at the other end. The function of these extension surfaces 40,41 will be described below.

The rod 35 of the actuator 34 is connected to the arm 36 at a point adjacent the pivot 37.

The fan motor 32 and the actuator 34 are powered from an electrical source (not shown) such as a battery or a mains source. The fan motor 32 and the actuator 34 are controlled by a control system 42 to operate as follows.

When the first form of fragrance disperser is initially switched on, power is supplied to the fan motor 32 and to the actuator 34. The fan motor 32 rotates the fan 17 in a clockwise direction as illustrated in FIG. 1 and, either before commencement of operation of the fan motor 32 or at the same time, the actuator rod 34 is moved by the actuator 34 to a first retracted position in which the shutter 38 is moved to the position shown in FIG. 1. In this position, the arcuate wall 39 forms a continuation of the arcuate wall 20 and provides a downstream continuation of the passage between the arcuate housing wall 20 and the outer periphery 19 of the fan 17 which increases in cross-section in a downstream direction. This provides a scrolled flowpath for air around the rotating fan 17. At the same time, the first extension surface 40 bears against the first side wall 14 while the second extension surface 41 engages the end of the second internal wall 24 adjacent the fan 17 to provide a continuation of the first passage. In this way, the first passage 21 is opened and the second passage 23 is closed so that air from the fan 17 passes through the first passage 21 to release fragrance from the wick 29 of the first fragrance bottle 25.

After a predetermined time has elapsed, during which time the fan motor 32 may be halted, the control system reverses the direction of rotation of the fan motor 32 and thus of the fan 17. At the same time, the actuator 34 is operated to extend the actuator rod 35 and move the shutter 38 from the first position shown in FIG. 1 to the second position shown in FIG. 2. In this position, the shutter 38 opens the second passage 23 and closes the first passage 21. The first extension surface 40 bears against the first side wall 14 while the second extension surface 41 engages the second interior wall 24 to form a continuation of the second passage 23. The arcuate shutter wall forms a downstream extension of the passage around the fan 17 which is of increasing cross-section in a downstream direction. Thus, air from the fan is diverted through the second passage 23 and past the wick 29 of the second fragrance container 26 while the first passage 21 is closed. This releases the second fragrance into the atmosphere.

Various modes of operation of a fragrance disperser of this general kind are described in our PCT Application GB 2002/004520.

Referring next to FIGS. 4-6, a second form of fragrance disperser has parts common with FIGS. 1 to 3. Those parts will be given the same reference numerals as the corresponding parts in FIGS. 1 to 3 and will not be described in detail.

In the second form of fragrance disperser, the actuator 34 is located adjacent the back wall 12 to one side of the fan 17 as seen in FIG. 6. An arm 45 is mounted intermediate its ends on a fixed pivot 46 for rotation about an axis parallel to the fan axis 18 and is provided at one end with a fork 47 and at the other end with a slot 48. The slot 48 receives a pin 49 on the rod 35 and extending normal to the length of the rod 35. The fork 47 engages a second pin 50 carried on a boss 51 formed centrally on a shutter 52. As seen in FIG. 6, the boss 51 includes a flange 53 that engages in a slot 54 formed in the housing 10 to constrain the shutter 52 to move in a rectilinear direction normal to the first and second side walls 14,15. The shutter 52 has an arcuate shutter wall 55 with a first extension surface 56 at one end and a second extension surface 57 at the other end. Of course, the connection between the arm 45 and the pin 50 on the boss 51 need not be via the fork 47. Any suitable connection, such as a slot, maybe used.

The housing 10 is modified by the replacement of the planar front wall 13 with an arcuate front wall 58 which forms not only the front wall but also the equivalent of the arcuate housing wall 20 of FIG. 1, as seen in FIGS. 4 and 5.

In use, the motor 32 and the actuator 34 are operated as described above. When the actuator rod 35 is in the first retracted position, the shutter 52 is in the position shown in FIG. 1 where the first end of the arcuate shutter wall 55 engages the second side wall 15 to close the second passage 23 and open the first passage 21. In this position, the second extension surface 57 engages the first interior wall 22 to form an extension of the first passage 21. In addition, the arcuate shutter wall 55 forms a continuation of the passage around the fan 15 providing a passage of increasing cross-section in a downstream direction. Thus air passes to the first fragrance bottle (omitted for clarity from FIGS. 4 to 6) to release fragrance while the second passage 23 is closed.

Reversal of the fan motor 32 and extension of the actuator rod 35 rotates the arm 45 around the pivot 46 with the fork 47 acting on the pin 50 to slide the boss 51 along the slot 54 to move the shutter 52 to the position shown in FIG. 5 where the shutter 52 closes the first passage 21 and opens the second passage 23 with the second extension surface engaging the second interior wall 24 and forming an extension of the second passage 23. In addition, the arcuate shutter wall 55 forms a continuation of the passage around the fan 17 that increases in cross-section in a downstream direction.

The effect of this is shown in FIG. 5 with the second passage 23 closed and the first passage 21 closed with the second passage 23 open. The end of the shutter wall 55 engages the first side wall 14 and the shutter wall forms a downstream extension of the passage around the fan 17 which decreases in cross-section in a downstream direction. The second extension surface 57 forms a continuation of the second passage 23. Accordingly, the air flow generated by the fan 17 passes along the second passage 23 where it releases fragrance from the wick 29 and passes the fragrance through the associated outlet 31.

The change in rotation of the motor 32 and the operation of the actuator 34 are controlled as described above.

Referring next to FIGS. 7 to 9, the third embodiment of the fragrance disperser has parts common with the second fragrance disperser. Those parts will be given the same reference numerals in the third fragrance disperser as in the second fragrance disperser and will not be described in detail.

In the third fragrance disperser, the actuator 34 is situated as described above with reference to FIGS. 4 to 6. However, the connection between the actuator rod 35 and the shutter 52 is formed by a pair of parallel arms 60,61. Each arm 60,61 is at one end formed integrally with the shutter 52 to provide respective hinges 62,63 between the shutter 52 and the arm 60,61. For example, the parts may be moulded together from a plastics material. The arms 60,61, at their ends opposite the shutter 52, are rotatably mounted on respective pivots 64,65 for rotation about respective axes parallel to the axis 18 of the fan 17. The arms 60,61 are parallel to one another. One arm 60 is formed with an extension 66 beyond the associated pivot 64 which is provided with a slot 67 receiving the pin 49 on the actuator rod 35.

The fragrance disperser of FIGS. 7 to 9 operates in a similar way to the fragrance disperser of FIGS. 4 to 6. When the actuator rod 35 is in the retracted position shown in FIG. 7, the shutter 52 closes the second passage 23 and opens the first passage 21 as described above. Movement of the actuator rod 35 to the extended position shown in FIG. 8 moves the shutter 52 to the position shown in FIG. 8 where the first passage 21 is closed and the second passage 23 is open. In contrast with the second form of the fragrance disperser, the shutter 52 in the third form of fragrance disperser is not guided in rectilinear movement between the position shown in FIG. 7 and FIG. 8. Rather, the shutter 52 is guided by the parallel arms 60,61.

Referring next to FIGS. 10 to 12, the fourth form of the fragrance dispersing device has parts common with the second and third forms of the fragrance disperser shown in FIGS. 4 to 6 and 7 to 9. Those parts will be given the same reference numerals in FIGS. 10 to 12 as they are in FIGS. 4 to 9 and will not be described in detail.

In the embodiment of FIGS. 10 to 12, the actuator 34 is located at a position somewhat spaced from the back wall 12 as seen in FIGS. 10, 11 and 12. The shutter 52 is formed in one piece with an arm 70 that extends in a generally radial direction relative to the centre of curvature of the arcuate shutter wall 55 and thus generally radially relative to the axis 18 of the fan 17. The arm 70 has an end remote from the shutter 52 rotatable about an axis parallel to the fan axis 18 about a fixed pivot 71. Intermediate its ends, the arm 70 is provided with an elongated slot 72 that engages the pin 49 on the actuator rod 35. The arm 70 is also provided with two L-shaped spring arms 74 projecting from respective opposite sides of the arm 70 for co-operation with two stops 73 provided on the casing 11 in a manner to be discussed below.

The fan motor 32 and the actuator 34 are operated as described above. When the actuator 34 is in the extended position shown in FIG. 10, the shutter 52 closes the second passage 23 and opens the first passage 21 so that fan air passes through the first passage 21 releasing fragrance. When the actuator rod 35 is moved to the retracted position shown in FIG. 11, the shutter 52 moves to the position shown in FIG. 11 where the first passage 21 is closed and the second passage 23 is opened so that fan air exits through the second passage 23 to release fragrance. As the arm 70 pivots in either sense one of the spring arms 74 engages a respective stop 73 to provide spring damping of the movement of the arm 70 to avoid noise due to vibration/rattling.

The use of a shutter 38,52 to control the release of two fragrances has been described above with reference to the drawings in relation to a fan that is reversible. It will be appreciated that the fan 17 need not be reversible; the fan 17 could provide a continuous supply of air on rotation in a single sense only and the shutters 38,52 simply open and close the first and second passages 21,23 with the arrangement of the passages 21,23 and the shutter 38,52 being altered accordingly. In addition, although, in the embodiments of FIGS. 1 to 12, the flow control of the air is performed by a shutter 38,52, it is possible to control the flow by means other than a shutter. For example, two separate shutters may be provided or the passages 21,23 may be opened and closed by other means such as louvres. In addition, although in the embodiments described above with reference to the drawings, the shutters 38,52 move between extreme positions, the shutters 38, 52, could move to one or more positions between the extreme positions to provide a required proportionate mixture of the fragrances.

The embodiments described above with reference to FIGS. 1 to 12 use an electronically operated actuator 34 which extends and retracts a rod 35. The actuator could take any other form including a hydraulic actuator or any other suitable form of actuator.

The invention claimed is:

1. A fragrance disperser comprising:
   first and second sources of fragrance,
   first and second flowpaths, each associated with a respective source of fragrance,
   a fan for providing a flow of air along the first and second flowpaths to release the associated fragrances, and
   a flow controller separate from the fan and movable by an actuator between a first position in which air flows along the first flowpath to allow release of the first fragrance and a second position in which air flows along the second flowpath to allow release of the second fragrance,
   wherein the fan is within a housing and the housing includes a chamber housing the fan and first and second passages leading from the housing and forming respectively the first and second flowpaths.

2. A disperser according to claim 1 wherein the first and second flowpaths comprise respective first and second passages, the flow controller opening the first passage and closing the second passage in the first position thereof and closing the first passage and opening the second passage in the second position thereof.

3. A disperser according to claim 2 wherein the first passage has an inlet end adjacent the fan and the second passage has an inlet end adjacent the fan, the flow controller opening and closing said inlet ends.

4. A fragrance disperser comprising:
   first and second sources of fragrance,
   first and second flowpaths, each associated with a respective source of fragrance,
   a fan for providing a flow of air along the first and second flowpaths to release the associated fragrances, and
   a flow controller separate from the fan and movable by an actuator between a first position in which air flows along the first flowpath to allow release of the first fragrance and a second position in which air flows along the second flowpath to allow release of the second fragrance,
   wherein the fan is rotatable in respective opposite first and second senses, rotation of the fan in the first sense passing air through the first flowpath with the flow controller in the first position and rotation of the fan in the second sense with the flow controller in the second position passing air through the second flowpath.

5. A disperser according to claim 4 and comprising control means for controlling the actuator and the fan so that the flow controller is in first position when the fan rotates in said first sense and the flow controller is in said second position when the fan rotates in said second sense.

6. A disperser according to claim 4 wherein the fan is within a housing, the housing including a wall extending around the fan and defining a path for air leading to the first flowpath and the second flowpath, the flow controller including a flow directing surface which, in both the first position and the second position, provides a downstream extension of said housing wall.

7. A disperser according to claim 6 wherein the fan has an outer periphery, the housing wall being arcuate about an axis co-axial with the axis of rotation of the fan, the flow directing surface being arcuate and forming, with the outer periphery of the fan, a passage of increasing cross-section in a downstream direction.

8. A disperser according to claim 6 wherein the flow controller includes a first extension surface which forms a continuation of the first flowpath when the flow controller is in said first position and a second extension surface which forms a continuation of the second flowpath when the flow controller is in said second position.

9. A disperser according to claim 1 wherein the chamber includes an arcuate wall partially surrounding the fan, the arcuate wall having a first end and a second end, the first passage leading from the first end of the arcuate wall and the second passage leading from the second end of the arcuate wall.

10. A disperser according to claim 1 wherein the first and second passages are side-by-side in the housing.

11. A disperser according to claim 1 wherein the actuator is electronically operated.

12. A disperser according to claim 1 wherein the flow controller in the first position prevents release of the second fragrance and in the second position prevents release of the first fragrance.

13. A fragrance dispenser comprising:
    first and second sources of fragrance,
    first and second flowpaths, each associated with a respective source of fragrance,
    a fan for providing a flow of air along the first and second flowpaths to release the associated fragrances, and
    a flow controller separate from the fan and movable by an actuator between a first position in which air flows along the first flowpath to allow release of the first fragrance and a second position in which air flows along the second flowpath to allow release of the second fragrance,
    wherein the flow controller is movable by the actuator to at least one position between said first and second positions to provide a proportionate increase of both fragrances.

14. A disperser according to claim 13 wherein said actuator is connected to the flow controller by a mechanism that translates operation of actuator into movement of the flow controller between said first and second positions.

15. A disperser according to claim 14 wherein the mechanism includes at least one arm connected between the flow controller and the actuator.

16. A disperser according to claim 15 wherein the actuator includes a rod movable between first and second positions to cause the at least one arm to move the flow controller between the first and second positions.

17. A disperser according to claim 16 wherein the at least one arm is pivotally mounted, movement of the rod rotating the at least one arm around the pivot.

18. A disperser according to claim 17 wherein the at least one arm has a first end and a second end, the first end being fixed to the flow controller and the second end being pivotally mounted, the rod acting on the arm intermediate the ends thereof.

19. A disperser according to claim 18 wherein the arm extends away from the fan in a generally radial direction.

20. A disperser according to claim 18 wherein the arm is pivoted to one side of the fan and the flow controller is on a diametrically opposite side of the fan, the arm extending across the fan.

21. A disperser according to claim 17 wherein the at least one arm has a first and a second end and is pivotally mounted intermediate the first and second ends, the first end being pivotally connected to the flow controller and the second end being pivotally connected to the rod.

22. A disperser according to claim 21 wherein the at least one arm extends away from the fan in a generally radial direction.

23. A disperser according to claim 16 wherein said at least one arm is one of two parallel arms, each arm having a first end and a second end, the first ends of the arms being pivotally connected to the flow controller and the second ends of the arms being connected to spaced fixed pivots, the rod acting on one of said arms.

24. A disperser according to claim 13 wherein the fan is within a housing, the housing including a chamber housing the fan and first and second passages leading from the housing and forming respectively the first and second flowpaths.

* * * * *

UNITED STATES PATENT AND TRADEMARK OFFICE
CERTIFICATE OF CORRECTION

| | |
|---|---|
| PATENT NO. | : 7,621,511 B2 |
| APPLICATION NO. | : 10/568069 |
| DATED | : November 24, 2009 |
| INVENTOR(S) | : Hayes-Pankhurst et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 626 days.

Signed and Sealed this

Twenty-sixth Day of October, 2010

David J. Kappos
*Director of the United States Patent and Trademark Office*